(12) United States Patent
Vergaelen et al.

(10) Patent No.: US 12,251,443 B2
(45) Date of Patent: *Mar. 18, 2025

(54) DRUG FORMULATIONS COMPRISING POLYOXAZOLINES AS MATRIX EXCIPIENT

(71) Applicant: Universiteit Gent, Ghent (BE)

(72) Inventors: Maarten Vergaelen, Gentbrugge (BE); Richard Hoogenboom, Terneuzen (BE); Victor Retamero de la Rosa, Ghent (BE); Chris Vervaet, Kachtem (BE); Aseel Samaro, Ghent (BE); Valérie Vanhoorne, Ghent (BE)

(73) Assignee: Universiteit Gent, Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/467,916

(22) Filed: Sep. 15, 2023

(65) Prior Publication Data
US 2024/0000943 A1    Jan. 4, 2024

Related U.S. Application Data

(63) Continuation of application No. 16/980,651, filed as application No. PCT/EP2019/056711 on Mar. 18, 2019, now Pat. No. 11,793,878.

(30) Foreign Application Priority Data

Mar. 16, 2018 (EP) ..................... 18162401

(51) Int. Cl.
A61K 47/34    (2017.01)
A61K 31/138    (2006.01)
A61K 31/155    (2006.01)
A61K 31/522    (2006.01)

(52) U.S. Cl.
CPC ............ *A61K 47/34* (2013.01); *A61K 31/138* (2013.01); *A61K 31/155* (2013.01); *A61K 31/522* (2013.01)

(58) Field of Classification Search
None
See application file for complete search history.

(56) References Cited

U.S. PATENT DOCUMENTS

2012/0183606 A1    7/2012  Mathias et al.
2013/0017166 A1*   1/2013  Kabanov .............. A61P 25/16
                                                       435/325

FOREIGN PATENT DOCUMENTS

| DE | 2020263 A1 | 11/1971 |
| WO | 2009156180 A2 | 12/2009 |
| WO | 2011002285 A1 | 1/2011 |
| WO | 2013097245 A1 | 7/2012 |
| WO | 2013103297 A1 | 7/2013 |
| WO | 2016008817 A1 | 1/2016 |

OTHER PUBLICATIONS

Claeys, Macromolecular Rapid Communications, 33, 19, 2012 (Year: 2012).*
International Search Report and Written Opinion mailed May 15, 2019, in reference to co-pending European Patent Application No. PCT/EP2019/056711 filed Mar. 18, 2019.
European Search Report in reference to co-pending European Patent Application No. 18162401.6 filed Aug. 17, 2018.
Claeys, et al., "Poly(2-ethyl-2-oxazoline) as Matrix Excipient for Drug Formulation by Hot Melt Extrusion and Injection Molding", Macromolecular Journals, vol. 33, pp. 1701-1707, 2012.
Oleszko-Torbus, et al., "Control of the Crystalline Properties of 2-Isopropyl-2-oxazoline Copolymers in Condensed State and in Solution Depending on the Composition", Macromolecules, pp. 7636-7645, 2017.
Raveendran, et al., "Poly(2-oxazoline) block copolymer nanoparticles for curcumin loading and delivery to cancer cells", European Polymer Journal, vol. 93, pp. 682-694, 2017.
Dordovic, et al., "Tuning of Thermoresponsivity of a Poly(2-alkyl-2-oxazoline) Block Copolymer by Interaction with Surface-Active and Chaotropic Metallacarborane Anion", Chemistry, an Asian Journal, vol. 13, pp. 838-845, 2018.
Seo, et al., "Poly(2-oxazoline) block copolymer based formulations of taxanes: effect of copolymer and drug structure, concentration, and environmental factors", Polymers Advanced Technology, vol. 26, pp. 837-850, 2015.

* cited by examiner

*Primary Examiner* — Robert A Wax
*Assistant Examiner* — William Craigo
(74) *Attorney, Agent, or Firm* — Dinsmore & Shohl LLP

(57) ABSTRACT

Polyoxazoline polymers, polymer combinations, and compositions comprising those polymers or combinations of polymers are disclosed. The invention further relates to the use of said polyoxazoline polymers, said combinations and compositions comprising such polymers and combinations for the sustained release of one or more active ingredients, in particular one or more active pharmaceutical ingredients. It further relates to the use of polyoxazoline polymers or polymer combinations as drug carrier.

20 Claims, 3 Drawing Sheets

DRUG FORMULATIONS COMPRISING POLYOXAZOLINES AS MATRIX EXCIPIENT

CROSS-REFERENCES TO RELATED APPLICATIONS

This application is a continuation of U.S. patent application Ser. No. 16/980,651, filed Sep. 14, 2020, which is a national-stage entry under 35 U.S.C. § 371 of International Application No PCT/EP2019/056711, filed Mar. 18, 2019, which International Application claims benefit of priority to European Patent Application 18126401.6, filed Mar. 16, 2018.

FIELD OF THE INVENTION

The present invention relates to polyoxazoline polymers, polymer combinations and (pharmaceutical) compositions comprising those polymers or combinations of polymers. The invention further relates to the use of said polyoxazoline polymers, said combinations and (pharmaceutical) compositions comprising such polymers and combinations for the sustained release of one or more active ingredients, in particular one or more active pharmaceutical ingredients. It further relates to the use of polyoxazoline polymers and polymer combinations as drug carrier. The present invention also discloses a process for manufacturing a (pharmaceutical) composition comprising said polyoxazoline polymers or combinations or polyoxazoline polymers.

BACKGROUND TO THE INVENTION

Oral solid dosage forms with sustained release are of high interest as they allow to maintain therapeutically optimal plasma drug concentrations for an extended period of time. Fluctuation of the drug plasma concentration caused by periodic drug administration is a major disadvantage of conventional oral drug delivery formulations which can result in toxic and/or sub-therapeutic levels. Toxic plasma levels can result in undesirable side effects while sub-therapeutic plasma levels can cause inefficient therapy as the drug plasma concentration is only shortly within the therapeutic window. These effects are even more pronounced for drugs with a small therapeutic window or drugs with a short half-life as these require multiple daily administrations. The latter can also compromise the patient compliance.

Although sustained release drug products offer many advantages, formulation of such drug products is challenging. A key aspect is achieving a suitable drug release rate to maintain the plasma levels within the therapeutic range over the desired time period. Development of sustained release formulations is especially challenging for highly dosed and highly soluble active pharmaceutical ingredients (API) as the drug release is often too fast and/or showing a burst release.

A wide variety of hydrophilic (e.g. hydroxypropylmethylcellulose, xanthan gum) and hydrophobic (e.g. methacrylic acid copolymers, ethylcellulose) controlled release polymers are available for formulation of sustained release oral dosage forms. Hydroxypropylmethylcellulose (HPMC) is currently by far the most commonly used polymer for sustained release as it allows relatively high drug loadings, is non-toxic, non-ionic, pH- and enzyme-resistant and can be processed via direct compression or wet granulation. Additionally, HPMC offers formulation flexibility as it is available in different grades, varying in molecular weight and substitution degree.

Although the sustained release effect is dependent on the API solubility, applied manufacturing technique, the polymer, the API/polymer ratio and various other formulation aspects, it is generally recognized that the drug release of formulations including maximum 40% (w/w) of drug load can be sustained over 24 h. Currently no commercially available polymers can ensure sustained drug release of highly soluble APIs with a drug load higher than 40% (w/w).

Polyoxazolines are promising candidates as non-toxic polymer carriers for (oral) drug delivery. They typically offer the advantages of a straightforward preparation, a good stability, a low toxicity and immunogenicity, large loading capacities, good hydrophilic and hydrophobic properties, thereby being highly tunable. Poly(2-oxazoline)s or poly(2-alkyl/aryl-2-oxazolines), are commonly abbreviated as PAOs, POx or POZ and are readily obtained via the cationic ring-opening polymerization of 2-oxazolines.

For example, WO2013103297 describes polyoxazoline polymers containing one or more pendant units with an amide group and the use of these polymers in the therapeutic prophylactic treatment or diagnosis of a disease or disorder. These polymers provide excellent delivery of small therapeutic molecules and biopharmaceuticals to the tissue involved. For example, it was demonstrated that commercially available poly(2-ethyl-2-oxazoline) (PEtOx, tradename Aquazol®) can act as protective excipient for solid dispersion of cannabinoids outperforming commercially available polymeric excipients (Plasdone® K90, Soluplus® and Eudragit® 100) with regard to cannabinoid stability, which has been disclosed in US20120183606.

However, up till now these polymers were unsuccessful in providing formulations for sustained release of pharmaceutical active agents, mainly due to the lack of sustained release capacity. Specifically, sustained release of hydrophilic drugs from oral formulations is challenging, but required for longer lasting actions.

In the present invention, we here provide novel and specific polyoxazoline polymers and polymer combinations (in particular blends) comprising poly(2-oxazolines) that are particularly useful for oral sustained release of one or more active ingredients, in particular one or more pharmaceutical active ingredients, such as for example the highly water soluble crystalline model drug metoprolol tartrate (MPT).

SUMMARY OF THE INVENTION

The present invention relates to a polymer combination, in particular blend, comprising two or more poly(2-oxazoline)s and compositions, in particular sustained release formulations, comprising such combinations/blends and an active ingredient. The invention also provides compositions, in particular sustained release formulations, comprising:

a homopolymer or copolymer containing at least one (2-$C_{3-5}$-alkyl-2-oxazoline) unit, or a polymer blend as defined herein in combination with an active ingredient.

Hence, in a particular embodiment, the sustained release formulations of the present invention may comprise one or more of the following:

a homopolymer containing at least one (2-$C_{3-5}$-alkyl-2-oxazoline) unit;

a copolymer containing at least one (2-$C_{3-5}$-alkyl-2-oxazoline) unit;

a polymer combination, in the form of a copolymer comprising at least one poly(2-$C_{3-5}$-alkyl-2-oxazoline)s a polymer combination, in the form of a blend comprising at least one poly(2-C$_{3-5}$-alkyl-2-oxazoline)s In particular, said poly(2-C$_{3-5}$-alkyl-2-oxazoline)s, said polymer combinations/blends and (pharmaceutical) compositions (e.g. sustained release formulations), are used for sustained release of active ingredients, preferably active pharmaceutical ingredients, even more preferably hydrophilic active pharmaceutical ingredients, such as for example metoprolol tartrate (MPT).

The present invention is particularly related to a polymer combination, preferably a blend, comprising two or more poly(2_oxazoline)s wherein at least 25% of said two or more poly(2-oxazolines) are poly(2-C$_{3-5}$-alkyl-2-oxazoline)s; in particular poly(2-C$_{3-5}$-alkyl-2-oxazoline)s wherein C$_3$-alkyl is selected from propyl and its isomers including cyclic isomers, C$_4$-alkyl is selected from butyl and its isomers including cyclic isomers, and C$_5$-alkyl is selected from pentyl and its isomers including cyclic isomers.

In a further embodiment, the present invention is related to a polymer combination, in particular blend, comprising two or more poly(2-oxazoline)s wherein at least 25% of the two or more poly(2-oxazoline)s are poly(2-C$_3$-alkyl-2-oxazoline)s.

In another embodiment, the present invention relates to a polymer combination, in particular blend, comprising two or more poly(2-oxazoline)s wherein at least 25% of the two or more poly(2-oxazoline)s are poly(2-C$_4$-alkyl-2-oxazoline)s.

In still another embodiment, the present invention relates to a polymer combination, in particular blend, comprising two or more poly(2-oxazoline)s wherein at least 25% of the two or more poly(2-oxazoline)s are poly(2C$_5$-alkyl-2-oxazoline)s.

In a further embodiment, the present invention discloses a polymer combination, in particular blend, comprising two or more poly(2-oxazolines) wherein at least 50% of the two or more poly(2-oxazolines) are poly(2-C$_{3-5}$-alkyl-2-oxazoline)s; in particular poly(2-C$_{3-5}$-alkyl-2-oxazoline)s wherein C$_3$-alkyl is selected from propyl and its isomers including cyclic isomers, C$_4$-alkyl is selected from butyl and its isomers including cyclic isomers, and C$_5$-alkyl is selected from pentyl and its isomers including cyclic isomers.

In a further embodiment, the present invention is related to a polymer combination, in particular blend, comprising two or more poly(2_oxazoline)s wherein at least 50% of the two or more poly(2-oxazoline)s are poly(2-C$_3$-alkyl-2-oxazoline)s.

In another embodiment, the present invention relates to a polymer combination, in particular blend, comprising two or more poly(2-oxazoline)s wherein at least 50% of the two or more poly(2-oxazoline)s are poly(2-C$_4$-alkyl-2-oxazoline)s.

In still another embodiment, the present invention relates to a polymer combination, in particular blend, comprising two or more poly(2-oxazoline)s wherein at least 50% of the two or more poly(2-oxazoline)s are poly(2C$_5$-alkyl-2-oxazoline)s.

In a further embodiment, the present invention relates to a polymer combination, in particular blend, wherein at least 25%; in particular at least 50% of the two or more poly(2-oxazoline)s are poly(2-C$_{4-5}$-alkyl-2-oxazoline)s; in particular wherein C$_4$-alkyl is selected from butyl and its isomers including cyclic isomers, and C$_5$-alkyl is selected from pentyl and its isomers including cyclic isomers.

In an even further embodiment, a polymer combination, in particular blend, is disclosed wherein at least 25%; in particular at least 50% of the two or more poly(2-oxazoline)s are poly(2-C$_4$-alkyl-2-oxazoline)s; in particular wherein C$_4$-alkyl is selected from butyl and its isomers including cyclic isomers.

In yet another embodiment, a polymer combination, in particular blend, is disclosed wherein at least 25%; in particular at least 50% of the two or more poly(2-oxazoline)s are poly(2C$_5$-alkyl-2-oxazoline)s; in particular wherein C$_5$-alkyl is selected from pentyl and its isomers including cyclic isomers.

In still a further embodiment, the C$_{3-5}$-alkyl- of the poly(2-C$_{3-5}$-alkyl-2-oxazoline)s in the polymer combination, in particular blend, of the present invention is selected from propyl, isopropyl, cyclopropyl, butyl, sec-butyl, isobutyl, tert-butyl, cyclobutyl, pentyl, tert-pentyl, neopentyl, isopentyl, sec-pentyl, 3-pentyl, or cyclopentyl.

Hence, more specifically, the C$_4$-alkyl of the poly(2-C$_{3-5}$-alkyl-2-oxazoline)s in the polymer combination, in particular blend, of the present invention is selected from butyl, sec-butyl, isobutyl, tert-butyl, or cyclobutyl; and the C$_5$-alkyl of the poly(2-C$_{3-5}$-alkyl-2_oxazoline)s in the polymer combination, in particular blends, of the present invention is selected from pentyl, tert-pentyl, neopentyl, isopentyl, sec-pentyl, 3-pentyl, or cyclopentyl.

In a further preferred embodiment, the polymer combination, in particular blend, comprises two or more poly(2-oxazolines) wherein at least 25%; in particular at least 50% of the poly(2-C$_{3-5}$-alkyl-2-oxazoline)s is poly(2-n-propyl-2-oxazoline).

In another further embodiment, the polymer combination, in particular blend, comprises two or more poly(2-oxazolines) wherein at least 25%; in particular at least 50% of the poly(2-C$_{3-5}$-alkyl-2-oxazoline)s is poly(2-sec-butyl-2-oxazoline).

In another embodiment, the polymer combination, in particular blend, comprises two or more poly(2-oxazolines) wherein maximum 75 weight % (wt %) of two or more poly(2-oxazolines) is poly(2-ethyl-2-oxazoline). In still a further embodiment, the polymer combination, in particular blend, of the present invention comprises two or more poly(2-oxazolines) wherein at least 50 wt % of the poly(2-C$_{3-5}$-alkyl-2-oxazoline)s is poly(2-n-propyl-2-oxazoline) and maximum 50 wt % of the two or poly(2-oxazolines) is poly(2-ethyl-2-oxazoline). In an even more preferred embodiment, the polymer combination, in particular blend, of the present invention comprises 50 wt % poly(2-n-propyl-2-oxazoline) and 50% poly(2-ethyl-2-oxazoline).

The present invention is further directed to a polymer combination, in particular blend, according to one or more of the previous embodiments wherein said polymer combination is selected from the list comprising a (polyoxazoline) blend or a polyoxazoline copolymer.

The present invention is also directed to a composition, in particular sustained release formulation, comprising:
 a homopolymer or copolymer containing at least one (2-C$_{3-5}$-alkyl-2-oxazoline) unit, or
 a polymer combination, in particular blend according to the different embodiments as described herein above;
 and one or more active ingredients, preferably one or more active pharmaceutical ingredients (API).

More preferably, said composition, in particular sustained release formulation, comprises:
 a homopolymer or copolymer containing at least one (2-C$_{3-5}$-alkyl-2-oxazoline) unit, or
 a polymer combination, in particular blend, according to the different embodiments of the invention;
 and one or more hydrophilic active pharmaceutical ingredients.

In another embodiment, the composition, in particular sustained release formulation, according to the present invention is combined with one or more active ingredients in a ratio between about 10:90 to about 80:20; more preferably in a ratio about 20:80 to about 70:30; most preferably in a ratio of about 30:70 to about 50:50.

Typical for the present invention, is that the composition according to the different embodiments of the invention is a sustained release composition, in particular a pharmaceutical sustained release composition wherein between 10-80% of the one or more active ingredients is released within the first 6 hours, and wherein no more than 75% of the one or more active ingredients is released in the first 120 min.

In another embodiment, between 10-80% of the one or more active ingredients is released within the first 8 hours and no more than 75% of the one or more active ingredients is released in the first 120 min.

In another embodiment, the composition according to the different embodiments of the invention is a sustained release composition wherein between 80-100% of the one or more active ingredients is released within the first 24 h and no more than 75% of the one or more active ingredients is released in the first 120 minutes. In an even further embodiment, the composition according to the different embodiments of the invention is a sustained release composition wherein between 10-80% of the one or more active ingredients is released within the first 6 hours, between of the one or more active ingredients is released within the first 24 h and no more than 75% of the one or more active ingredients is released within the first 120 minutes.

In still another embodiment, the composition according to the different embodiments of the invention is a sustained release composition wherein between 10-80% of the one or more active ingredients is released within the first 8 hours, between 80-100% of the one or more active ingredients is released within the first 24 h and no more than 75% of the one or more active ingredients is released within the first 120 minutes.

The composition, in particular sustained release formulation, according to the different embodiments of the present invention is manufactured by common formulation methods including but not limited to hot melt extrusion, injection moulding, direct compression, melt granulation or a combination of those. In a preferred embodiment, the compositions are manufactured by direct compression or injection moulding.

In yet another embodiment, the polymer combination, in particular blend, or the compositions, in particular sustained release formulations, according to the different embodiments of the invention are for use as a human or veterinary medicine.

In a further aspect, the present invention is directed to the use of the composition, in particular sustained release formulation, of the different embodiments of the present invention for the sustained release of one or more active ingredients, in particular one or more active pharmaceutical ingredients. In a more preferred embodiment, the use of the composition, in particular sustained release formulation, according to the different embodiments of the invention for sustained release of one or more hydrophilic active pharmaceutical ingredients is disclosed.

Further, also a process for manufacturing the composition, in particular sustained release formulation, according to this invention is disclosed. Said process comprises mixing one or more active ingredients with a homopolymer or copolymer containing at least one (2-$C_{3-5}$-alkyl-2-oxazoline) unit; or the polymer combination (preferably blend), according to the different embodiments of the invention, followed by common formulation methods including but not limited to hot melt extrusion, injection moulding, direct compression, melt granulation, or a combination of those.

In a particular embodiment, the homopolymer or copolymer containing at least one (2-$C_{3-5}$-alkyl-2-oxazoline) unit or the polymer combination, in particular blend, according to the invention and the one or more active ingredients are all in powder form.

In another embodiment of the invention, the use of one or more poly(2-$C_{3-5}$-alkyl-2-oxazoline)s, homopolymers containing at least one (2-$C_{3-5}$-alkyl-2-oxazoline) unit, copolymer containing at least one (2-$C_{3-5}$-alkyl-2-oxazoline) unit, or polymer combinations, in particular blends, according to the different embodiments of the invention as a drug carrier for sustained release of one or more active ingredients is disclosed. In a further embodiment, said one or more active ingredients are one or more active pharmaceutical ingredients; even further one or more hydrophilic active pharmaceutical ingredients.

In a further embodiment, the use of said one or more poly(2-$C_{3-5}$-alkyl-2-oxazoline)s, homopolymers containing at least one (2-$C_{3-5}$-alkyl-2-oxazoline) unit, copolymer containing at least one (2-$C_{3-5}$-alkyl-2-oxazoline) unit, or the polymer combinations, in particular blends, according to the different embodiments of the invention, as a drug carrier for sustained release of active ingredients is further characterized in that in said use, the one or more poly(2-$C_{3-5}$-alkyl-2-oxazoline)s, homopolymers containing at least one (2-$C_{3-5}$-alkyl-2-oxazoline) unit, copolymer containing at least one (2-$C_{3-5}$-alkyl-2-oxazoline) unit, or polymer combinations, in particular blends, are combined with one or more active ingredients in a PAOx:active ingredient ratio between about 10:90 to about 80:20; more preferably in a ratio about 20:80 to about 70:30; most preferably in a ratio of about 30:70 to about 50:50.

In a particular embodiment, the present invention provides combinations, blends and formulations as defined herein, comprising at least 50 wt % of active agent; in particular at least 60 wt %; even more in particular at least 70 wt %. In the context of the present invention, the wt % is calculated over the total composition of the combinations, blends and formulations as defined herein. Hence, a combination, blend or formulation defined herein as comprising at least 50 wt % of active agent, is considered to further comprise a maximum of 50 wt % of other components such as the polymers, combinations and blends as defined herein.

In another aspect, the use of one or more poly(2-$C_{3-5}$-alkyl-2-oxazoline)s, homopolymers containing at least one (2-$C_{3-5}$-alkyl-2-oxazoline) unit, copolymer containing at least one (2-$C_{3-5}$-alkyl-2-oxazoline) unit, or the polymer combinations, in particular blends, according to the different embodiments of the invention as a drug carrier for sustained release of active ingredients according to the different embodiments of the invention is further characterized in that the drug carrier and the one or more active ingredients are combined using common formulation methods including but not limited to hot melt extrusion, direct compression, injection moulding, melt granulation or a combination of those; preferably using direct compression or injection moulding.

In still another embodiment, the use of one or more poly(2-$C_{3-5}$-alkyl-2-oxazoline)s, homopolymers containing at least one (2-$C_{3-5}$-alkyl-2-oxazoline) unit, copolymer containing at least one (2-$C_{3-5}$-alkyl-2-oxazoline) unit, or the polymer combinations, in particular blends, according to the different embodiments of the invention as a drug carrier for sustained release of active ingredients according to the different embodiments of the invention is further characterized in that between 10-80% of the one or more active ingredients is released within the first 6 hours and no more than 75% of the one or more active ingredients is released within the first 120 minutes.

In another embodiment, 10-80% of the one or more active ingredients is released with the first 8 hours and no more than 75% of the one or more active ingredients is released within the first 120 minutes.

In another embodiment, between 80-100% of the one or more active ingredients is released within the first 24 h and no more than 75% of the one or more active ingredients is released within the first 120 minutes.

In an even more preferred embodiment, between 10-80% of the one or more active ingredients is released within the first 6 hours, between 80-100% of the one or more active ingredients is released within the first 24 h and no more than 75% of the one or more active ingredients is released within the first 120 minutes.

In a further preferred embodiment, between 10-80% of the one or more active ingredients is released within the first 8 hours, between 80-100% of the one or more active ingredients is released within the first 24 h and no more than 75% of the one or more active ingredients is released within the first 120 minutes.

As already outlined herein above, the present invention is directed to particular poly(2-$C_{3-5}$-alkyl-2-oxazoline)s, particular polymer combinations, blends, compositions, in particular sustained release formulations, and the use of said poly(2-$C_{3-5}$-alkyl-2-oxazoline)s, homopolymers containing at least one (2-$C_{3-5}$-alkyl-2-oxazoline) unit, copolymer containing at least one (2-$C_{3-5}$-alkyl-2-oxazoline) unit, and polymer combinations, in particular blends, as a drug carrier for sustained release of one or more active ingredients, in particular one or more active pharmaceutical ingredients; even more preferably, hydrophilic active pharmaceutical ingredients.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
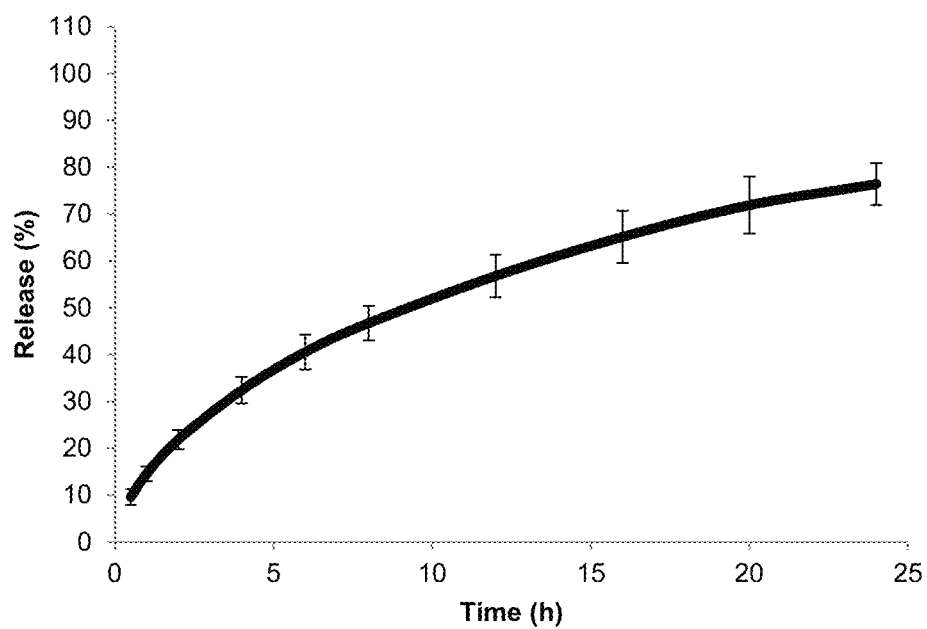
FIG. 1: In vitro drug release from direct compressed tablets (n=3) with 70% w/w anhydrous theophylline and 30% w/w PnPrOx.

The current invention provides a polymer combination, in particular blend, comprising two or more poly(2-oxazoline)s wherein at least 25% of the two or more poly(2-oxazoline)s are poly(2-$C_{3-5}$-alkyl-2-oxazoline)s, and a composition, in particular sustained release formulation, comprising said combination (in particular blend), homopolymers containing at least one (2-$C_{3-5}$-alkyl-2-oxazoline) unit or copolymer containing at least one (2-$C_{3-5}$-alkyl-2-oxazoline) unit, useful for sustained release of one or more active ingredients, in particular one or more active pharmaceutical ingredients, even more in particular one or more hydrophilic active pharmaceutical ingredients.

In the present invention the poly(2-$C_{3-5}$-alkyl-2-oxazoline)s are represented by the following general formula:

wherein X is —$C_{3-5}$ alkyl-:

The present invention is related to a polymer combination, in particular blend,

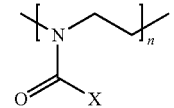

comprising two or more poly(2-oxazolines) wherein at least 25%; in particular at least 50% of the two or more poly(2-oxazoline)s are poly(2-$C_{3-5}$-alkyl-2-oxazoline)s.

In the light of the present invention, the term "alkyl" by itself or as part of another substituent can refer herein to fully unsaturated, partially unsaturated and fully saturated hydrocarbons. Alkyl groups may be linear or branched and may be substituted as indicated herein. When a subscript is used herein following a carbon atom, the subscript refers to the number of carbon atoms that the named group may contain. Thus, for example, $C_{1-4}$ alkyl means an alkyl of one to four carbon atoms. In general, examples of alkyl groups are methyl, ethyl, n-propyl, i-propyl, butyl, and its isomers (e.g. n-butyl, i-butyl, sec-butyl and t-butyl); pentyl and its isomers (e.g. tert-pentyl, neopentyl, isopentyl, sec-pentyl, 3-pentyl, or cyclopentyl).

In the light of the present invention, $C_3$-$C_5$ alkyl includes all linear, branched or cyclic alkyl groups with between 3 and 5 carbon atoms, and thus includes propyl, isopropyl, cyclo-propyl, butyl, sec-butyl, isobutyl, tert-butyl, cyclobutyl, pentyl, tert-pentyl, neopentyl, isopentyl, sec-pentyl, 3-pentyl, or cyclopentyl.

In a further embodiment, the polymer combination, in particular blend, of the present invention comprises two or more poly(2-oxazolines) wherein at least 25%; in particular at least 50% of the two or more poly(2-oxazoline)s are poly(2-$C_{4-5}$-alkyl-2-oxazoline)s. In an even further embodiment, the polymer combination, in particular blend, of the present invention comprises two or more poly(2-oxazolines) wherein at least 25%; in particular at least 50% of the two or more poly(2-oxazoline)s are poly(2-$C_4$-alkyl-2-oxazoline)s, wherein $C_4$-alkyl is selected from butyl and its isomers including cyclic isomers. In another further embodiment, the polymer combination, in particular blend, of the present invention comprises two or more poly(2-oxazolines) wherein at least 25%; in particular at least 50% of the two or more poly(2_oxazoline)s are poly(2C$_5$-alkyl-2-oxazoline)s, wherein C$_5$-alkyl- is selected from pentyl and its isomers including cyclic isomers.

In a further preferred embodiment, the polymer combination, in particular blend, comprises two or more poly(2-oxazolines) wherein at least 25%; in particular, at least 50% of the poly(2-oxazolines) is poly(2-n-propyl-2-oxazoline), such as represented by the following general formula:

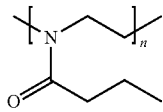

In another embodiment, the polymer combination, in particular blend, comprises two or more poly(2-oxazolines) wherein maximum 75 weight % (wt %) of the two or more poly(2-oxazoline)s is poly(2-ethyl-2-oxazoline), such a represented by the following general formula:

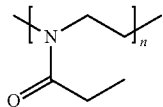

The poly(2-oxazoline)s as used in the present invention preferably have a number average molar mass as between 10,000 g/mol and 200,000 g/mol; preferably between 40,000 g/mol and 200,000 g/mol. In a preferred embodiment, the poly(2-C$_{3-5}$-alkyl-2-oxazlone)s as used in the different embodiments of the invention have a number average molar mass between 10,000 g/mol and 200,000 g/mol; preferably between 40,000 g/mol and 200,000 g/mol. In an even more preferred embodiment, the poly(2-C$_{4-5}$-alkyl-2-oxazoline)s have a number average molar mass as between 10,000 g/mol and 200,000 g/mol; preferably between 40,000 g/mol and 200,000 g/mol.

In still a further embodiment, the polymer combination, in particular blend, of the present invention comprises two or more poly(2-oxazolines) wherein at least 50 wt % of the poly(2-C$_{3-5}$ alkylxazolines) is poly(2-n-propyl-2-oxazoline) and maximum 50 wt % of the poly(2-oxazolines) is poly(2-ethyl-2-oxazoline). In an even more preferred embodiment, the polymer combination, in particular blend, of the present invention comprises 50 wt % poly(2-n-propyl-2-oxazoline) and 50 wt % poly(2-ethyl-2-oxazoline).

In another embodiment of the invention, the polymer combination, in particular blend, according to the invention may also comprise other excipients in addition to the poly (2-oxazoline)s. These other excipients can be polymer excipients selected from the list including, but not limited to, hydroxyproplylmethylcellulose, xanthan gum, methacrylic acid copolymers, ethylcellulose, or polyvinylpyrrolidon.

However, the presence of these other excipients is not essential for the polymer combination, in particular blend, or composition, in particular sustained release formulation, according to the present invention. Hence, in a specific embodiment, the present invention provides a polymer combination, in particular blend, or composition, in particular sustained release formulation, as claimed herein which does not comprise further excipients or components other than the enclosed polymers and (where applicable) active ingredients.

The present invention is also directed to a polymer combination, in particular blend, according to one or more of the previous embodiments wherein said polymer combination is selected from the list comprising a (polyoxazoline) polymer blend or a polyoxazoline copolymer. A blend as used herein is considered as a polymer mixture in which the at least two polymers are blended. A polyoxazoline polymer blend as used herein is considered as a polymer mixture in which the at least two polymers are blended, and wherein the two or more poly(2-C$_{3-5}$-alkyl-2-oxazoline)s polymers are blended together. In a preferred embodiment, all components of the blend are in powder form.

A polyoxazoline copolymer as used herein is considered as a copolymer comprising said two or more poly(2-C$_{3-5}$-alkyl-2-oxazoline)s. In another embodiment, other poly(2-oxazoline)s, such as poly(2-ethyl-2-oxazoline) or poly(2-methyl-2-oxazoline) can be present as well in the copolymer.

In a preferred embodiment, the one or more polyoxazolines in the polymer combination, in particular blend, have a DP (degree of polymerization) of at least 100 and a dispersity of less than 1.6. As a result, the polymer combination, in particular blend, can be combined with (highly) water-soluble and/or crystalline active ingredient. Further, they preferably have a glass transition temperature of 30° C. or higher.

The "degree of polymerization" is the average number of monomeric units (i.e. n in the above formulae) in a polymer. The "dispersity" is a measure for the molar mass distribution, thus a measure of the heterogeneity of lengths/molar masses of polymer molecules in a given mixture.

As already indicated herein before, it was an object of this invention to also provide a composition, in particular sustained release formulation, comprising:

a homopolymer or copolymer containing at least one (2-C$_{3-5}$-alkyl-2-oxazoline) unit, or a polymer combination, in particular blend according to the different embodiments of the invention and one or more active ingredients, in particular one or more active pharmaceutical ingredients, even more in particular one or more hydrophilic active pharmaceutical ingredients.

In a specific embodiment, the composition, in particular sustained release formulation, comprises:

a copolymer containing at least one (2-C$_{3-5}$-alkyl-2-oxazoline) unit and at least one (2-methyl-2-oxazoline) unit, or a copolymer containing at least one (2-C$_{3-5}$-alkyl-2-oxazoline) unit and at least one (2-ethyl-2-oxazoline) unit, or a copolymer containing at least one (2-C$_{3-5}$-alkyl-2-oxazoline) unit and at least one (2-methyl-2-oxazoline) and/or (2-ethyl-2-oxazoline) unit, and one or more active ingredients, in particular one or more active pharmaceutical ingredients, even more in particular one or more hydrophilic active pharmaceutical ingredients.

Active ingredients according to the invention can include pharmaceutical ingredients, nutrients, cosmeceuticals, diagnostic agents, and nutritional agents.

The active ingredients that may be administered using the formulations, systems and methods of the invention are not limited, as the invention enables the effective delivery of a wide variety of active ingredients, in particular hydrophilic active ingredients.

The term active pharmaceutical agent as used herein refers to therapeutic, diagnostic, or prophylactic pharmaceutical and veterinary agents as well as other agents. In an another embodiment, the active pharmaceutical ingredient and also the pharmaceutical composition, in particular sustained release formulation, according to the different embodiments of the invention is for use as a human or veterinary medicine.

The one or more active pharmaceutical ingredients can be selected from any of the various classes of such ingredients including, but not limiting to, analgesic agents, anesthetic agents, anti-anginal agents, anti-arthritic agents, anti-arrhytmic agents, anti-asthmatic agents, antibacterial agents, anti-BPH agents, anticancer agents, anticholinergic agents, anticoagulants, anticonvulsants, antidepressants, antidiabetic agents, antidiarrheals, anti-epileptic agents, antifungal agents, antigout agents, antihelminthic agents, antihistamines, antihyperstensive agents, anti-inflammatory agents, antimalarial agents, antimigraine agents, antimuscarinic agents, antinauseants, antineoplastic agents, anti-obesity agents, anti-osteoporosis agents, antiparkinsonism agents, antiprotozola agents, antipruritics, antipsychotic agents, antipyretics, antispasmodics, antithyroid agents, antitubercular agents, antiulcer agents, anti-urinary incontinence agents, antiviral agents, anxiolytics, appetite suppressants, attention deficit disorder (ADD) and attention deficit hyperactivity disorder (ADHD) drugs, calcium channel blockers, cardiac inotropic agents, beta-blockers, central nervous system stimulants, cognition enhancers, corticosteroids, COX-2 inhibitors, decongestants, diuretics e.g. hydrochlorothiazide (HCT), gastro-intestinal agents, genetic material, histamine receptor antagonists, homonolytics, hypnotics, hypoglycemic agents, immunosuppressants, keratolytics, leukotriene inhibitors, lipid-regulating agents, macrolides, mitotic inhibitors, muscle relexants, narcotic antagonists, neuroleptic agents, nicotene, nutritional oils, parasympatholytic agents, sedatices, sex hormones, sympathomimetic agents, tranquilizers, vasodilators, vitamins, and combinations thereof.

In a specific embodiment, the active pharmaceutical ingredients of the present invention are hydrophilic (i.e. soluble in water and other polar substances), for example selected from metoprolol tartrate (MPT), metformin hydrochloride (MTF), and theophylline anhydrous (Theo).

The composition according to the different embodiments of the invention is typically characterized in that it is a sustained-release composition, in particular a composition wherein between 10-80% of the one or more active ingredients is released within the first 6 hours and wherein no more than 75% of the one or more active ingredients is released within the first 120 minutes.

In another embodiment, the composition according to the different embodiments of the invention is typically characterized in that it is a sustained-release composition, in particular a composition wherein between 10-80% of the one or more active ingredients is released within the first 8 hours and wherein no more than 75% of the one or more active ingredients is released within the first 120 minutes.

In yet another embodiment, about 80-100% of the one or more active ingredients is released within the first 24 hours and no more than 75% of the one or more active ingredients is released within the first 120 minutes.

In still a further embodiment, the composition according to the different embodiments of the invention is a sustained-release composition wherein between 10-80% of the one or more active ingredients is released within the first 6 hours, no more than 75% of the one or more active ingredients is released within the first 120 minutes and between 80-100% of the one or more active ingredients is released within the first 24 hours.

In still another further embodiment, the composition according to the different embodiments of the invention is a sustained-release composition wherein between 10-80% of the one or more active ingredients is released within the first 8 hours, no more than 75% of the one or more active ingredients is released within the first 120 minutes and between 80-100% of the one or more active ingredients is released within the first 24 hours.

As used herein, "controlled or sustained-release" refers to the release of an active ingredient from a pharmaceutical dosage form at a predetermined rate. Controlled or sustained release implies that the majority of the active ingredient does not "burst" off of the dosage form upon contact with a biological environment. On the other hand, "immediate release" implies that the majority of the drug is released from the dosage form upon contact with a biological environment.

If desired, the composition, in particular sustained release formulation, of the present invention can be combined with pharmaceutical excipients to produce pharmaceutical dosage forms, such as one or more fillers, pigments, colorants, flavourings, binders, plasticizers, antioxidants, lubricants, permeability enhancers, solid diluents and/or liquid diluents.

In a preferred embodiment, the composition, in particular sustained release formulation, or the combination, in particular blend, according to the different embodiments of the invention is in a solid dosage form. Solid dosage forms are preferably in the form of tablets, coated tablets, powders, powders of reconstitution, pellets, beads, mini-tablets, film coated tablets, bilayered tablets, tablet in tablet, pills, micropellets, small tablet units, MUPS, desintegrating tablets, dispersible tablets, granules, and microspheres, multiparticulates, capsules (filled with powders, powders for reconstitution, pellets, beads, mini-tablets, pills, micro-pellets, small tablet units, MUPS, orally disintegrating MUPS, granules, microspheres, multiparticulates), sachets (filled with powders, pellets, beads, mini-tablets, pills, micro-pellets, small tablet units, MUPS, disintegrating tablets, dispersible tablets, modified release tablets or capsules, granules, and microspheres, multiparticulates) and sprinkles and the like. Solid (dosage) forms as used in the present invention are not meant to encompass for example micellar compositions such as for examples disclosed in Raveendran et al., 2017.

In a preferred embodiment, the composition, in particular sustained release formulation, according to the different embodiments of the present invention is used for oral dosage.

In a particular embodiment, the polymer combination, in particular blend, or composition, in particular sustained release formulation, according to the different embodiments of the invention is characterized in that the active ingredient and the polymer combination, in particular blend, or poly (2-$C_{3-5}$-alkyl-2-oxazolines), homopolymers containing at least one (2-$C_{3-5}$-alkyl-2-oxazoline) or copolymers containing at least one (2-$C_{3-5}$-alkyl-2-oxazoline) unit are all in powder form and wherein a dry mixture is formed. In a further specific embodiment, no covalent linkages occur between the active ingredient and the poly(2-oxazoline)s in the composition, in particular sustained release formulation.

As already outlined herein above, with the present invention a polymer combination, in particular blend, and composition, in particular sustained release formulation, are provided for sustained-release of active ingredients, such as for example highly water soluble active pharmaceutical ingredients. A particular advantage of the present invention is that the polymer combination, in particular blend, and compositions, in particular sustained release formulations, are particularly suitable for oral delivery, which is a challenge because of reduced solubility of the different compounds in the formulations.

Another advantage of the present invention, is that the poly(2-$C_{3-5}$-alkyl-2-oxazoline)s as used in the polymer combination, in particular blend, or composition, in particular sustained release formulation, of the present invention allow very high drug loading. As a result, the release period of the active ingredients can be accurately tuned by the selection of the poly(2-$C_{3-5}$-alkyl-2-oxazoline)s and combining specific poly(2-oxazoline)s with the active ingredient.

The present invention is also directed a process for manufacturing the composition, in particular sustained release formulation, according to the different embodiments of the invention. In said process, one or more active ingredients are mixed with a poly(2-$C_{3-5}$-alkyl-2-oxazoline) a homopolymer containing at least one (2-$C_{3-5}$-alkyl-2-oxazoline) unit, a copolymer containing at least one (2-$C_{3-5}$-alkyl-2-oxazoline) unit; or with the polymer combination, in particular blend, according to the different embodiments of the invention, followed by common formulation methods including but not limited hot melt extrusion, injection moulding, direct compression, melt granulation or a combination of these. The preferred formulation method is dependent from the different compounds present in the polymer combination, in particular blend or compositions, in particular sustained release formulations. Preferably, direct compression or injection moulding is applied.

A hot melt extrusion process comprises the steps of preparing a melt of one or more active ingredients and the poly(2-$C_{3-5}$-alkyl-2-oxazoline), homopolymer containing at least one (2-$C_{3-5}$-alkyl-2-oxazoline) unit, a copolymer containing at least one (2-$C_{3-5}$-alkyl-2-oxazoline) unit or with the polymer combination, in particular blend, according to the invention, and cooling the melt until it solidifies. Melting usually involves heating above the softening point, i.e. glass transition temperature of the polymer. Usually, the melt temperature is in the range of about 50° C. to about 200° C. In some circumstances, the applied temperature should not be too high to not cause melting or decomposition of the active pharmaceutical ingredient.

Suitable extruders include single screw extruders, intermeshing screw extruders or else multiscrew extruders, preferably twin screw extruders, which can be co-rotating or counter-rotating and, optionally, be equipped with kneading disks.

The extrudates can be in the form of beads, granulates, tubes, strands or cylinders and these can be further processed into any desired shape.

By using any of the known formulation methods, the composition may be shaped as needed according to the desired mode of administration, for example films, tablet, pills, lozenges, sand capsules.

The present invention also provides the use of one or more poly(2-$C_{3-5}$-alkyl-2-oxazoline)s, homopolymer containing at least one (2-$C_{3-5}$-alkyl-2-oxazoline) unit, a copolymer containing at least one (2-$C_{3-5}$-alkyl-2-oxazoline) unit or a polymer combination, in particular blend, according to the different embodiments of the invention as a drug carrier for sustained release of active ingredients, in particular active pharmaceutical ingredients, even more in particular hydrophilic active pharmaceutical ingredients.

As already indicated above, sustained-release is considered as release of the active ingredients wherein between 10-80% of the one or more active ingredients is released within the first 6 hours and wherein no more than 75% of the one or more active ingredients is released within the first 120 minutes.

In yet another embodiment, sustained release is considered as release of active ingredients wherein about 80-100% of the one or more active ingredients is released within the first 24 hours and no more than 75% of the one or more active ingredients is released within the first 120 minutes.

In still a further embodiment, sustained-release is considered as release of active ingredients wherein between 10-80% of the one or more active ingredients is released within the first 6 hours, no more than 75% of the one or more active ingredients is released within the first 120 minutes and between 80-100% of the one or more active ingredients is released within the first 24 hours.

EXAMPLES

The purification and polymer synthesis methodologies in the below examples were performed as reported by Monnery et al. who reported a method for the preparation of uniform, high molar mass cyclic imino ether polymers (WO2016008817 A1).

Monomer Synthesis and Purification

2-Ethyl-2-oxazoline (EtOx; Polymer Chemistry Innovations) was purified via fractional distillation and purification over barium oxide. 2-n-Propyl-2-oxazoline (nPrOx) and 2-sec-butyl-2-oxazoline (secButOx) were synthesized via the Witte-Seeliger method (Witte et al., Ann. Chem. 1974), from their corresponding nitrile, i.e. butyronitrile and 2_methylbutyronitrile, respectively. The purification of nPrOx and secButOx was carried out similarly to that of EtOx. Finally, an additional distillation after drying over molten sodium was applied.

Solvent

The polymerizations were carried out in chlorobenzene (PhCl) as solvent. IPhCl was purified via consecutive washing steps with concentrated H2SO4, saturated NaHCO3(aq) and water. Drying was done over magnesium sulphate and final drying over CaH2. Afterwards a fractional distillation was performed.

Initiator

2-Phenyl-2-oxazolinium tetrafluoroborate (HPhOx-BF 4) salt was used as initiator for the polymerization. In short, the salt was obtained as a crystalline precipitate upon addition of 2-phenyl-2-oxazoline (PhOx) in a methanolic HBF 4 (50 wt %) solution. After recrystallization the salt was stored in a vacuum oven at 50° C., 10-1 mbar.

Polymerization

All polymers were synthesized with a target molar mass of 50,000 g/mol, according to the detailed procedure as reported in WO2016008817 A1. The only difference was in the scale (200 g versus 1 g) at which the synthesis has been performed. The polymerization details for the synthesis of 50,000 g/mol PEtOx, 50,000 g/mol, PnPrOx and 50,000 g/mol PsecButOx are summarized in Table 1.

TABLE 1

Overview of all reagents and experimental conditions for the synthesis of PAOx polymers used in the formulations. All polymerizations were performed at 60° C.

| Polymer type | MW (theor.) (DP/kDa) | Initiator (g) | Solvent (type/mL) | Monomer (conc./mL) | Reaction time (days) | Scale (g) |
|---|---|---|---|---|---|---|
| PEtOx_50kDa | 500/50 | 1.003 | PhCl/322.5 | 4.8/305.1 | 5 | 200 |
| PnPrOx_50kDa | 443/50 | 1.006 | PhCl/238.6 | 4.8/312.5 | 5.5 | 200 |
| PsecButOx_50kDa | 394/50 | 1.407 | PhCl/190.0 | 4.8/300 | 6 | 200 |

Polymer characterization was performed by size-exclusion chromatography (SEC), on an Agilent 1260-series HPLC system equipped with a 1260 online degasser, a 1260 ISO-pump, a 1260 automatic liquid sampler (ALS), a thermo-stated column compartment (TCC) at 50° C. equipped with two PLgel 5 μm mixed-D columns in series, a 1260 diode array detector (DAD) and a 1260 refractive index detector (RID). The used eluent is N,N-dimethylacetamide (DMA) containing 50 mM of lithium chloride at an optimized flow rate of 0.5 mL/min. The spectra were analyzed using the Agilent ChemStation software with the GPC add on. Molar mass (M n and M p) and dispersity (Đ) values were calculated against polymethylmethacrylate molar mass standards from PSS.

The characterization data for the synthesized polymers is summarized in Table 2.

TABLE 2

Overview size-exclusion chromatography data for the PAOx polymers used for SRF.

| Batch | $M_n$ (PMMA) kDa | $M_p$ (PMMA) kDa | Đ |
|---|---|---|---|
| PEtOx_50 kDa | 84.7 ± 0.6 * | 93.0 ± 4 * | 1.13 ± 0.02 * |
| PnPrOx_50 kDa | 65.9 ± 4.3 * | 81.4 ± 1.8 * | 1.14 ± 0.04 * |
| PsecButOx_50 kDa | 25.6 | 35.0 | 1.22 |

* Standard deviation provided for polymerizations performed in triplicate.

Example 1

Formulation:
  70% w/w anhydrous theophylline+30% w/w PnPrOx

Methods: Physical mixture was directly compressed using a compaction simulator (styl'one evolution, Medelpharm, France) equipped with cylindrical flat-faced Euro B punches of 10 mm diameter. Tablets (250 mg) were compressed using 10 kN compression force without pre-compression.

In vitro drug release: Drug release from the direct compressed tablets (n=3) was determined using the paddle method on a VK 7010 dissolution system (VanKel Industries, New Jersey, USA) with a speed of 100 rpm. Phosphate buffer (pH 6.8) was used as dissolution medium (900 mL) at 37±0.5° C. Samples were withdrawn at predetermined time points (0.5; 1; 2; 4; 6; 8; 12; 16; 20 and 24 h) and spectrophotometrically (UV-1650PC, Shimadzu Benelux, Antwerp, Belgium) analysed at a wavelength of 273 nm (FIG. 1).

Example 2

Formulation:
  70% w/w anhydrous theophylline+22.5% w/w PnPrOx+7.5% w/w PEtOx

Methods: Physical mixture was directly compressed using a compaction simulator (Styl'one evolution, Medelpharm, France) equipped with cylindrical flat-faced Euro B punches of 10 mm diameter. Tablets (250 mg) were compressed using 10 kN compression force without pre-compression.

Figure 2:
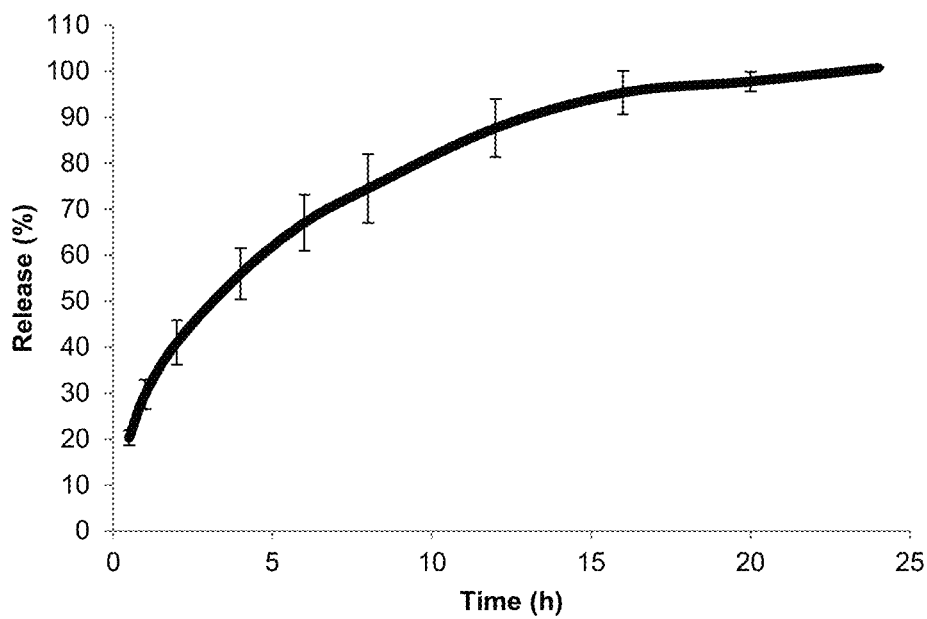
FIG. 2: In vitro drug release from direct compressed tablets (n=3) with 70% w/w anhydrous theophylline, 22.5% w/w PnPrOx and 7.5% w/w PEtOx.

In vitro drug release: Drug release from the direct compressed tablets (n=3) was determined using the paddle method on a VK 7010 dissolution system (VanKel Industries, New Jersey, USA) with a speed of 100 rpm. Phosphate buffer (pH 6.8) was used as dissolution medium (900 mL) at 37±0.5° C. Samples were withdrawn at predetermined time points (0.5; 1; 2; 4; 6; 8; 12; 16; 20 and 24 h) and spectrophotometrically (UV-1650PC, Shimadzu Benelux, Antwerp, Belgium) analysed at a wavelength of 273 nm (FIG. 2).

Example 3

Formulation:
  70% w/w metoprolol tartrate+30% w/w PSecBuOx

Methods: The physical mixture (70% drug load, w/w) was extruded using a co-rotating twin-screw extruder (Xplore microcmpounder, DSM, The Netherlands), operating at a screw speed of 100 rpm and processing temperature of 110° C. After HME, the extrudates were processed into tablets via injection moulding (Haake MiniJet System, Thermo Electron, Karlsruhe, Germany) at a temperature of 110° C. During the injection moulding process, the material was forced into the mold using an injection pressure of 800 bar (during 10 s). A post-pressure of 400 bar (during 5 s) was applied to avoid expansion by relaxation of the polymer. The temperature of the mold was set at 20° C.

Figure 3:
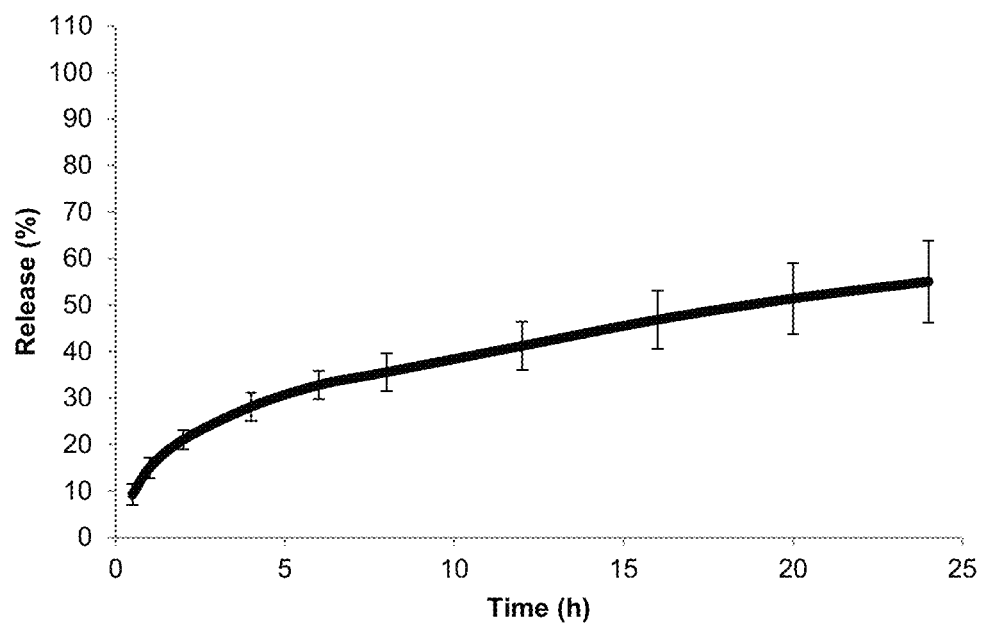
FIG. 3: In vitro drug release from injection-moulded tablets (n=3) with 70% w/w metoprolol tartrate and 30% w/w PSecBuOx.

In vitro drug release: Drug release from the injection-moulded tablets (n=3) was determined using the paddle method on a VK 7010 dissolution system (VanKel Industries, New Jersey, USA) with a speed of 100 rpm. Phosphate buffer (pH 6.8) was used as dissolution medium (900 mL) at 37±0.5° C. Samples were withdrawn at predetermined time points (0.5; 1; 2; 4; 6; 8; 12; 16; 20 and 24 h) and spectrophotometrically (UV-1650PC, Shimadzu Benelux, Antwerp, Belgium) analysed at a wavelength of 223 nm (FIG. 3).

Example 4

Formulation:
  70% w/w metformin.HCl+30% w/w PSecBuOx

Methods: The physical mixture (70% drug load, w/w) was extruded using a co-rotating twin-screw extruder (Xplore microcmpounder, DSM, The Netherlands), operating at a screw speed of 100 rpm and processing temperature of 140° C. After HME, the extrudates were processed into tablets via injection moulding (Haake MiniJet System, Thermo Electron, Karlsruhe, Germany) at a temperature of 180° C. During the injection moulding process, the material was forced into the mold using an injection pressure of 800 bar (during 10 s). A post-pressure of 400 bar (during 5 s) was applied to avoid expansion by relaxation of the polymer. The temperature of the mold was set at 20° C.

Figure 4:
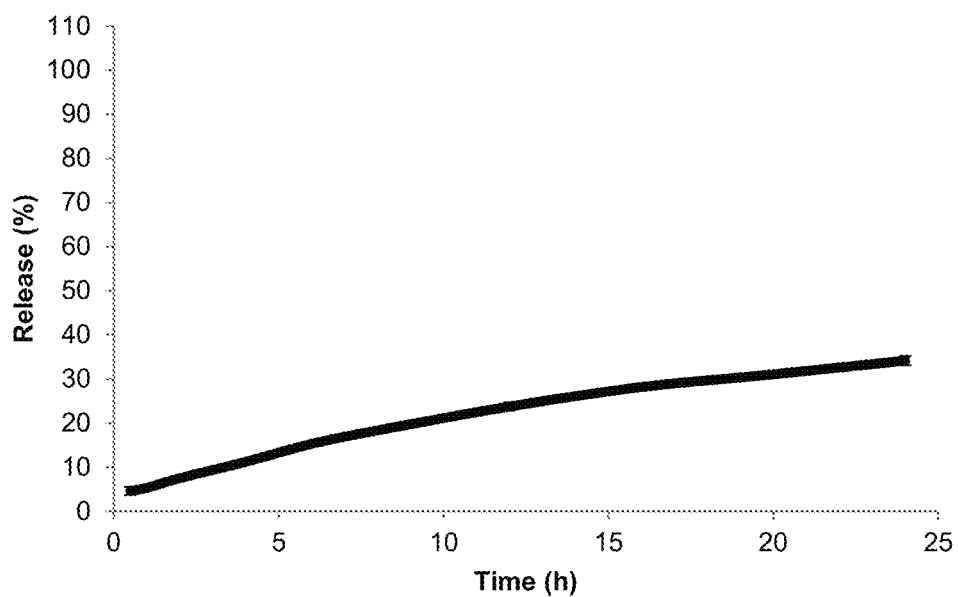
FIG. 4: In vitro drug release from injection-moulded tablets (n=3) with 70% w/w metformin·HCl and 30% w/w PSecBuOx.

In vitro drug release: Drug release from the injection-molded tablets (n=3) was determined using the paddle method on a VK 7010 dissolution system (VanKel Industries, New Jersey, USA) with a speed of 100 rpm. Phosphate buffer (pH 6.8) was used as dissolution medium (900 mL) at 37±0.5° C. Samples were withdrawn at predetermined time points (0.5; 1; 2; 4; 6; 8; 12; 16; 20 and 24 h) and spectrophotometrically (UV-1650PC, Shimadzu Benelux, Antwerp, Belgium) analysed at a wavelength of 234 nm (FIG. 4).

Example 5

Formulation:
70% w/w metoprolol tartrate+22.5% w/w PSecBuOx+7.5% w/w PEtOx

Methods: The physical mixture (70% drug load, w/w) was extruded using a co-rotating twin-screw extruder (Xplore microcmpounder, DSM, The Netherlands), operating at a screw speed of 100 rpm and processing temperature of 100° C. After HME, the extrudates were processed into tablets via injection moulding (Haake MiniJet System, Thermo Electron, Karlsruhe, Germany) at a temperature of 110° C. During the injection moulding process, the material was forced into the mold using an injection pressure of 800 bar (during 10 s). A post-pressure of 400 bar (during 5 s) was applied to avoid expansion by relaxation of the polymer. The temperature of the mold was set at 20° C.

Figure 5:
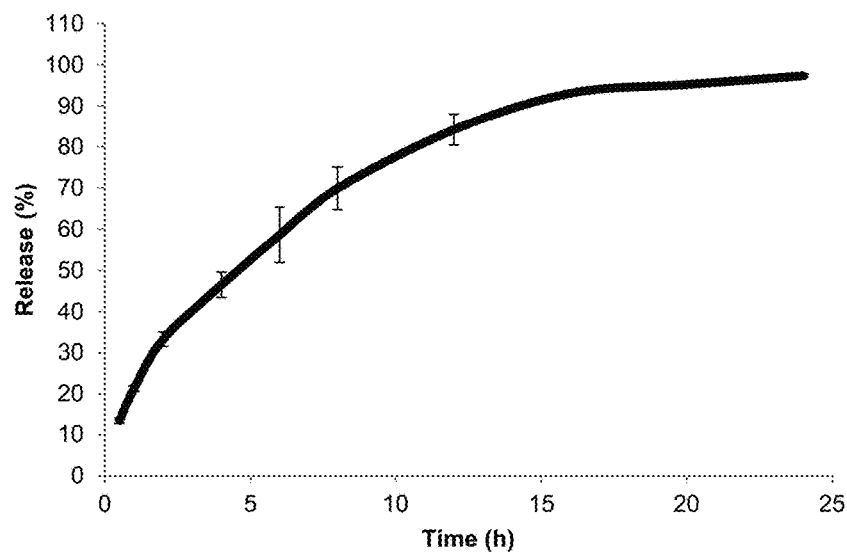
FIG. 5: In vitro drug release from injection-moulded tablets (n=3) with 70% w/w metoprolol tartrate, 22.5% w/w PSecBuOx and 7.5% w/w PEtOx.

In vitro drug release: Drug release from the injection-moulded tablets (n=3) was determined using the paddle method on a VK 7010 dissolution system (VanKel Industries, New Jersey, USA) with a speed of 100 rpm. Phosphate buffer (pH 6.8) was used as dissolution medium (900 mL) at 37±0.5° C. Samples were withdrawn at predetermined time points (0.5; 1; 2; 4; 6; 8; 12; 16; 20 and 24 h) and spectrophotometrically (UV_1650 PC, Shimadzu Benelux, Antwerp, Belgium) analysed at a wavelength of 223 nm (FIG. 5).

Example 6

Formulation:
25% w/w Metoprolol Tartrate+75% w/w PEtOx
50% w/w Metoprolol Tartrate+50% w/w PEtOx Methods: The physical mixtures were extruded using a co-rotating twin-screw extruder (Haake MiniLab II Micro Compounder, Thermo Electron), operating at 100 rpm screw speeds and processing of (120-145°) C temperature. After HME, the extrudates were processed into tablets via injection moulding (Haake MiniJet System, Thermo Electron, Karlsruhe, Germany) at a temperature of (120-145)° C. During the injection moulding process, the material was forced into the mold using an injection pressure of 880 bar (during 10 s). A post-pressure of 400 bar (during 5 s) was applied to avoid expansion by relaxation of the polymer. The temperature of the mold was set at 20° C.

Figure 6A:
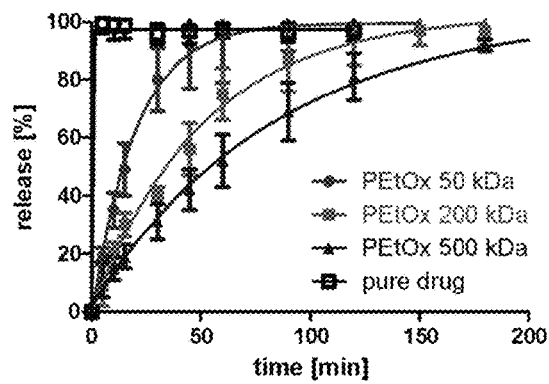
FIGS. 6A and 6B: In vitro drug release from injection-moulded tablets (n=3) with 25% w/w metoprolol tartrate and 75% w/w PEtOx (FIG. 6A) or 50% w/w metoprolol tartrate and 50% w/w PEtOx (FIG. 6B).
Figure 6B:
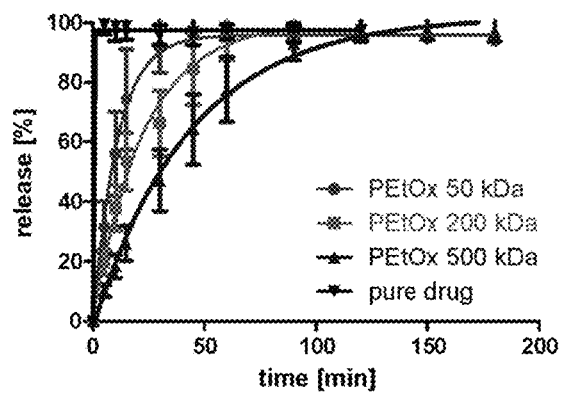

In vitro drug release: Drug release from the injection-moulded tablets (n=3) was determined using the paddle method on a VK 7010 dissolution system (VanKel Industries, New Jersey, USA) at a speed of 100 rpm. Hydrochloric acid (pH 1) and phosphate buffer (pH 7) was used as dissolution medium (900 mL) at 37±0.5° C. Samples were withdrawn at predetermined time points and spectrophotometrically analyzed for API concentration at their specific wavelength of maximum absorbance. Cumulative release curves show the dissolution of MPT from HME/IM PEtOx tablets using PEtOx of different molecular weight. In (FIG. 6A) the drug load was 25 wt % while in (FIG. 6B) the drug load was 50 wt %. (Macromol Rapid Commun. 2012,33 (19):1701-7).

What is claimed is:

1. A method of providing a sustained release of an active ingredient to a human or veterinary subject in need thereof, the method comprising:
   administering a sustained release formulation to the human or veterinary subject, the sustained release formulation comprising:
   at least one active ingredient; and
   a polymer blend comprising at least two poly(2-oxazoline)s, wherein at least 75% by weight of the at least two poly(2-oxazoline)s are poly(2-$C_{3-5}$-alkyl-2-oxazoline)s.

2. The method of claim 1, wherein the sustained release formulation is further defined in that, as determined in vitro using the paddle method, not more than 75% of the at least one active ingredients are released within the first 120 minutes.

3. The method of claim 1, wherein the at least two poly(2-oxazoline)s are at least 75% by weight poly(2-$C_{4-5}$-alkyl-2-oxazoline)s.

4. The method of claim 1, wherein the at least two poly(2-oxazoline)s are at least 75% by weight poly(2-n-propyl-2-oxazoline).

5. The method of claim 1, wherein the at least one active ingredient comprises a hydrophilic active ingredient.

6. The method of claim 1, wherein the sustained release formulation comprises greater than 50% by weight hydrophilic active ingredient, based on the total weight of the sustained release formulation.

7. The method of claim 6, wherein the hydrophilic active ingredient is selected from the group consisting of metoprolol tartrate, metformin hydrochloride, theophylline anhydrous, and combinations thereof.

8. A method of providing a sustained release of a hydrophilic active ingredient to a human or veterinary subject in need thereof, the method comprising:
   administering a sustained release formulation to the human or veterinary subject, the sustained release formulation being in a solid dosage form and comprising:
   more than 50% by weight of a hydrophilic active ingredient or combination of hydrophilic active ingredients, based on the total weight of the sustained release formulation; and
   a polymer blend comprising at least two poly(2-oxazoline)s, wherein at least 25% of the at least two poly(2-oxazoline)s are poly(2-$C_{3-5}$-alkyl-2-oxazoline)s.

9. The method of claim 8, wherein the sustained release formulation is further defined in that, as determined in vitro using the paddle method, not more than 75% of the at least one active ingredients are released within the first 120 minutes.

10. The method of claim 8, wherein the sustained release formulation comprises greater than 70% by weight hydrophilic active ingredient.

11. The method of claim 8, wherein the one or more hydrophilic active ingredients are selected from metoprolol tartrate, metformin hydrochloride, and theophylline anhydrous.

12. The method of claim 8, wherein the at least two poly(2-oxazoline)s are at least 50% by weight poly(2-C$_{3-5}$-alkyl-2-oxazoline)s.

13. The method of claim 8, wherein the at least two poly(2-oxazoline)s are at least 75% by weight poly(2-C$_{3-5}$-alkyl-2-oxazoline)s.

14. The method of claim 8, wherein the at least two poly(2-oxazoline)s are at least 75% by weight poly(2-C$_{4-5}$-alkyl-2-oxazoline)s.

15. The method of claim 8, wherein the at least two poly(2-oxazoline)s are at least 75% by weight poly(2-n-propyl-2-oxazoline).

16. A method of providing a sustained release of a hydrophilic active ingredient to a human or veterinary subject in need thereof, the method comprising:
    administering a sustained release formulation to the human or veterinary subject, the sustained release formulation being in a solid dosage form and comprising:
       more than 50% of a hydrophilic active ingredient selected from metoprolol tartrate, metformin hydrochloride, and theophylline anhydrous, or a combination thereof, based on the total weight of the sustained release formulation; and
       a polymer blend comprising at least two poly(2-oxazoline)s, wherein at least 75% of the at least two poly(2-oxazoline)s are poly(2-C$_{3-5}$-alkyl-2-oxazoline)s.

17. The method of claim 16, wherein the sustained release formulation is further defined in that, as determined in vitro using the paddle method, not more than 75% of the at least one active ingredients are released within the first 120 minutes.

18. The method of claim 16, wherein the at least two poly(2-oxazoline)s are at least 75% by weight poly(2-C$_{4-5}$-alkyl-2-oxazoline)s.

19. The method of claim 16, wherein the at least two poly(2-oxazoline)s are at least 75% by weight poly(2-n-propyl-2-oxazoline).

20. The method of claim 16, wherein the sustained release formulation is administered to the human or veterinary subject orally.

* * * * *

UNITED STATES PATENT AND TRADEMARK OFFICE
CERTIFICATE OF CORRECTION

PATENT NO. : 12,251,443 B2
APPLICATION NO. : 18/467916
DATED : March 18, 2025
INVENTOR(S) : Maarten Vergaelen et al.

It is certified that error appears in the above-identified patent and that said Letters Patent is hereby corrected as shown below:

In the Specification

In Column 3, Line(s) 12, delete "poly(2_oxazoline)s" and insert --poly(2-oxazoline)s--, therefor.

In Column 3, Line(s) 32 & 33, delete "poly(2C$_5$-alkyl-2-oxa-zoline)s." and insert --poly(2-C$_5$-alkyl-2-oxazoline)s.--, therefor.

In Column 3, Line(s) 46, delete "poly(2_oxazoline)s" and insert --poly(2-oxazoline)s--, therefor.

In Column 3, Line(s) 56 & 57, delete "poly(2C$_5$-alkyl-2-oxa-zoline)s." and insert --poly(2-C$_5$-alkyl-2-oxazoline)s.--, therefor.

In Column 4, Line(s) 7, delete "poly(2C$_5$-alkyl-2-oxa-zoline)s" and insert --poly(2-C$_5$-alkyl-2-oxazoline)s--, therefor.

In Column 5, Line(s) 27, after "between", insert --80-100%--.

In Column 9, Line(s) 3, delete "poly(2_oxazoline)s" and insert --poly(2-oxazoline)s--, therefor.

In Column 9, Line(s) 3 & 4, delete "poly(2C$_5$-alkyl-2-oxazo-line)s," and insert --poly(2-C$_5$-alkyl-2-oxazoline)s,--, therefor.

In Column 9, Line(s) 59, delete "hydroxyproplylmethylcellulose" and insert --hydroxypropylmethylcellulose--, therefor.

In Column 9, Line(s) 60, delete "polyvinylpyrrolidon" and insert --polyvinylpyrrolidone--, therefor.

In Column 11, Line(s) 15 & 16, delete "anti-arrhyt-mic" and insert --anti-arrhythmic--, therefor.

Signed and Sealed this
Eleventh Day of November, 2025

John A. Squires
*Director of the United States Patent and Trademark Office*

CERTIFICATE OF CORRECTION (continued)
U.S. Pat. No. 12,251,443 B2

In Column 11, Line(s) 21, delete "antihyperstensive" and insert --antihypertensive--, therefor.

In Column 11, Line(s) 25, delete "antiprotozola" and insert --antiprotozoal--, therefor.

In Column 11, Line(s) 38, delete "relexants" and insert --relaxants--, therefor.

In Column 11, Line(s) 39, delete "nicotene" and insert --nicotine--, therefor.

In Column 11, Line(s) 40, delete "sedatices" and insert --sedatives--, therefor.

In Column 12, Line(s) 37, delete "desintegrating" and insert --disintegrating--, therefor.

In Column 13, Line(s) 19, after "directed", insert --to--.